United States Patent
Sakai et al.

(10) Patent No.: US 10,022,092 B2
(45) Date of Patent: Jul. 17, 2018

(54) X-RAY CT APPARATUS AND GANTRY DEVICE

(71) Applicant: TOSHIBA MEDICAL SYSTEMS CORPORATION, Otawara-Shi (JP)

(72) Inventors: Satoshi Sakai, Otawara (JP); Takeo Nabatame, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 218 days.

(21) Appl. No.: 14/919,929

(22) Filed: Oct. 22, 2015

(65) Prior Publication Data

US 2016/0120485 A1    May 5, 2016

(30) Foreign Application Priority Data

Oct. 31, 2014    (JP) .................................. 2014-223516
Oct. 5, 2015    (JP) .................................. 2015-197748

(51) Int. Cl.
*A61B 6/00*    (2006.01)
*A61B 6/03*    (2006.01)
*A61B 6/10*    (2006.01)

(52) U.S. Cl.
CPC .............. *A61B 6/032* (2013.01); *A61B 6/107* (2013.01); *A61B 6/461* (2013.01); *A61B 6/486* (2013.01)

(58) Field of Classification Search
CPC ....... A61B 6/032; A61B 6/461; A61B 6/4435; A61B 6/08; A61B 6/542
USPC ......................... 378/4–20, 114–116, 193–198
See application file for complete search history.

(56) References Cited

U.S. PATENT DOCUMENTS

| 2014/0098934 A1* | 4/2014 | Kondo | A61B 6/032 378/20 |
| 2014/0119494 A1* | 5/2014 | Youn | A61B 6/032 378/4 |
| 2015/0245804 A1* | 9/2015 | Kieft | A61B 6/06 378/147 |

FOREIGN PATENT DOCUMENTS

| JP | 2002-200072 | 7/2002 |
| JP | 2005-066037 | 3/2005 |
| JP | 2005-095663 | 4/2005 |
| JP | 2009-268793 | 11/2009 |
| JP | 2010-162385 | 7/2010 |

* cited by examiner

*Primary Examiner* — Courtney Thomas
(74) *Attorney, Agent, or Firm* — Oblon, McClelland, Maier & Neustadt, L.L.P.

(57) ABSTRACT

According to one embodiment, an X-ray CT apparatus includes an X-ray source, an X-ray detector, processing circuitry, a showing device, an image processing circuit, and a gantry device. The X-ray source irradiates an object with X-rays. The X-ray detector detects X-rays radiated by the X-ray source and passed through the object. The processing circuitry sets an irradiation section, which is a moving section of the X-ray source or the X-ray detector during X-ray irradiation. The showing device displays the irradiation section. The image processing circuit generates an X-ray CT image based on data obtained by the X-ray detector during the X-ray irradiation through the irradiation section. The gantry device is provided with the X-ray source, the X-ray detector, and the showing device.

19 Claims, 12 Drawing Sheets

X-RAY CT APPARATUS AND GANTRY DEVICE

CROSS-REFERENCE TO RELATED APPLICATIONS

This application claims the benefit of priority of Japanese Patent Application No. 2014-223516, filed Oct. 31, 2014, and Japanese Patent Application No. 2015-197748, filed Oct. 5, 2015, the entire contents of all of which are incorporated herein by reference.

FIELD

Embodiments described herein relate generally to an X-ray CT (Computed Tomography) apparatus and a gantry device.

BACKGROUND

An operator of medical services, who operates an X-ray CT apparatus to image an object such as a patient, sometimes punctures a needle in paracentesis and attaches his or her hand in order to prevent the object from moving during a scan. An operator takes appropriate action to avoid his or her exposure so that direct rays from an X-ray tube are not directed to him or herself, and also has to pay attention to indirect exposure of scattered rays caused by scattered X-rays which were irradiated on an object.

In an X-ray CT apparatus, a half scan is known as a technique to acquire data of one volume of CT image to be reconstructed. In a half scan, X-rays are irradiated while rotating the X-ray emission source around an object by 180 degrees plus a fan angle. Exposure of a half scan is smaller than exposure of a scan over whole of a rotational orbit. However, exposure in a half scan changes according to the relationship between the standing point of an operator and the irradiation section of X-rays on the rotational orbit.

Some of conventional X-ray CT apparatuses display a scanned image of an object and an image of an estimated irradiation range of X-rays by superimposing one of them on the other, in order to check whether the exposure range of the object includes a needless region or not. However, in such a conventional X-ray CT apparatus, it is impossible to recognize which span on the rotational orbit X-rays are irradiated during a half scan. Thus, in such a conventional X-ray CT apparatus, it is impossible to determine the standing position where exposure to an operator is minimized and the position where an operator attaches his or her hand.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray CT apparatus and a gantry device according to embodiments of the present invention with reference to the drawings.

In general, according to one embodiment, the X-ray CT apparatus includes an X-ray source, an X-ray detector, processing circuitry, a showing device, an image processing circuit, and a gantry device. The X-ray source irradiates an object with X-rays. The X-ray detector detects X-rays radiated by the X-ray source and passed through the object. The processing circuitry sets an irradiation section which is a moving span of the X-ray source or the X-ray detector during X-ray irradiation. The showing device displays the irradiation section. The image processing circuit generates an X-ray CT image based on data obtained by the X-ray detector during the X-ray irradiation through the irradiation section. The gantry device is provided with the X-ray source, the X-ray detector, and the showing device.

First Embodiment

Configuration of an X-ray CT apparatus and a gantry device of the first embodiment will be explained. The X-ray CT apparatus 100 of the first embodiment receives input of an irradiation section during which X-rays are irradiated on the rotational orbit of an X-ray tube, via a gantry input circuit 18, and displays the irradiation section on a showing device 19. Hereinafter, each component of the X-ray CT apparatus 100 of the first embodiment will be first explained, and then the gantry input circuit 18 and the showing device 19 will be explained in detail.

Figure 1:
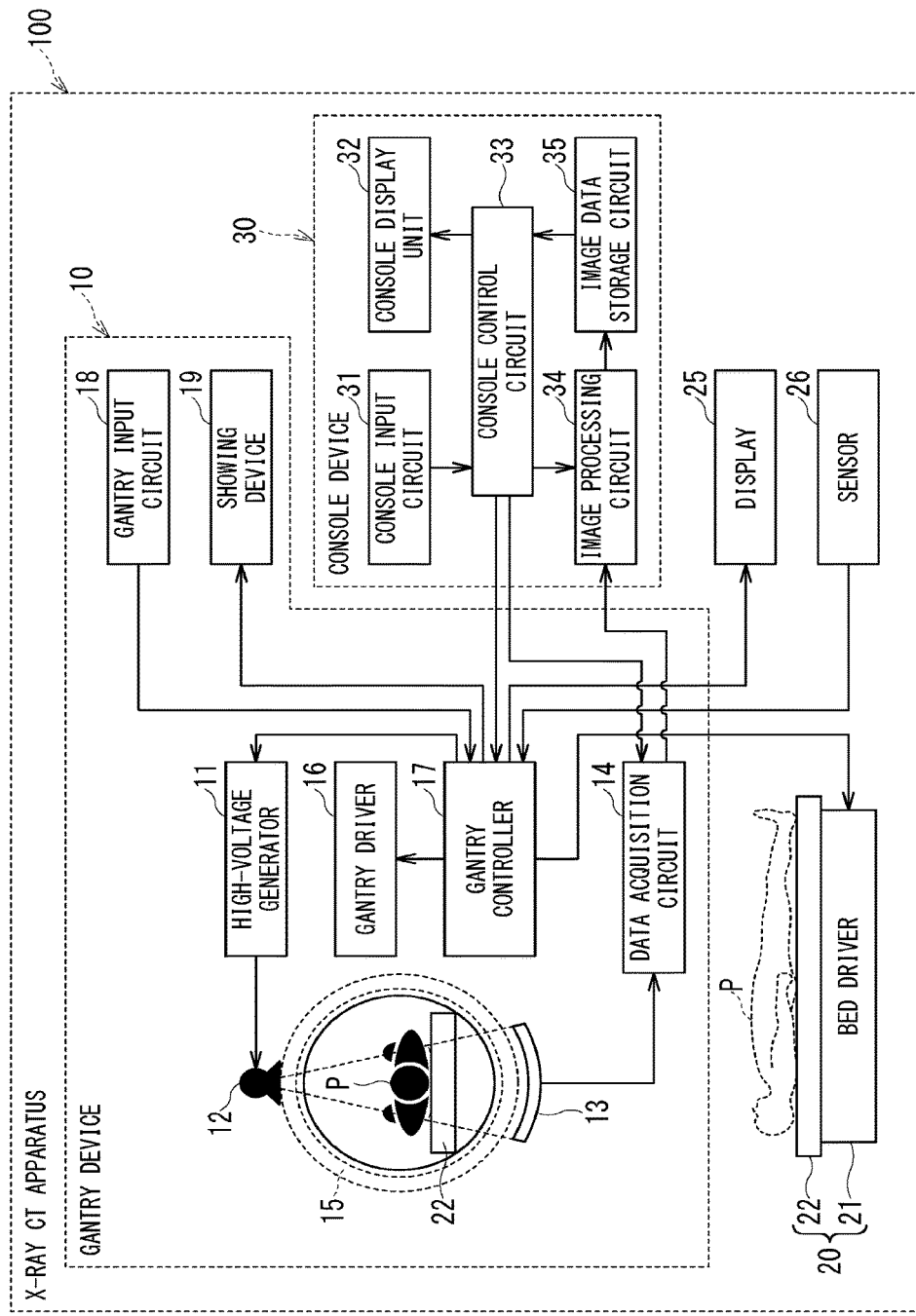
FIG. 1 is a block diagram showing an example of configuration of an X-ray CT apparatus of the first embodiment.

FIG. 1 is a block diagram showing an example of configuration of the X-ray CT apparatus 100 of the first embodiment. The X-ray CT apparatus 100 of the first embodiment includes a gantry device 10, a bed device 20, and a console device 30. The gantry device 10 and the bed device 20 are installed in a CT imaging room (examination room). On the other hand, the console device 30 is installed, for example, in an operators room which is a room separated from the CT imaging room.

The gantry device 10 is a device which irradiates the object P with X-rays, detects X-rays passing through the object P, and outputs the detected X-rays to the console device 30. Specifically, the gantry device 10 includes a high-voltage generator 11, an X-ray tube 12, an X-ray detector 13, a data acquisition circuit 14, a rotational frame 15, a gantry driver 16, a gantry controller 17, the gantry input circuit 18, and the showing device 19.

The high-voltage generator 11 supplies high voltage to the X-ray tube 12 under the control of the gantry controller 17. The X-ray tube 12 is a vacuum tube, is supplied the high voltage from the high-voltage generator 11, generates X-rays, and irradiates the object P with X-rays. The X-ray detector 13 detects X-rays which have passed through the object P. The data acquisition circuit 14 generates projection data based on the X-rays detected by the X-ray detector 13. The rotational frame 15 is an annular frame, and supports the X-ray tube 12 and the X-ray detector 13 so that the object P is interposed between the X-ray tube 12 and the X-ray detector 13.

Incidentally, there are various types of X-ray CT apparatuses. One of them is a rotate/rotate type which is configured so that an X-ray tube and an X-ray detector integrally rotate around an object. Another of them is a stationary/rotate type which is configured so that multiple detecting elements are arrayed in a ring-like state and only the X-ray source rotates around an object. Another of them is a type which is configured so that the position of an X-ray source is electronically moved by deflecting an electronic beam. The configuration of each of the embodiments of the present invention described below can be applied to any type of X-ray CT apparatus.

By appropriately replacing the X-ray tube 12 with an X-ray source, the embodiments of the present invention can be applied to the type of using an electronic beam. In the present specification, the X-ray CT apparatus 100 as a rotate/rotate type in which the X-ray tube 12 and the X-ray detector 13 integrally rotate around the object P has been explained above as an example.

The gantry driver 16 drives the gantry device 10 under the control of the gantry controller 17. Specifically, the gantry driver 16 continuously rotates the X-ray tube 12 and the X-ray detector 13 on a circular orbit whose center is the position of the object P, by driving a motor to continuously rotate the rotational frame 15 at high speed.

The gantry controller 17 includes processing circuitry and memory circuit. The processing circuitry of the gantry controller 17 is a processor implementing an imaging control function of controlling the high-voltage generator 11, the gantry driver 16, and the bed driver 21, by executing programs stored in the memory circuit under the control of the console control circuit 33 to be described below.

The gantry input circuit 18 receives input of an irradiation section of X-rays. This irradiation section determines which span on the rotational orbit of the X-ray tube 12 X-rays are irradiated. In addition, the showing device 19 is configured of a general display and/or light emitting devices such as plural LEDs (Light Emitting Diodes), and displays the irradiation section by displaying an image on the display or controlling the lighting state of each of the light emitting devices. As to the gantry input circuit 18 and the showing device 19, they will be explained in detail below.

Incidentally, an operator who operates the console input circuit 31 and the gantry input circuit 18 includes a surgeon who performs a medical treatment such as a surgical operation on the object P, in addition to an inspection engineer. A surgeon performs a medical treatment on the object P by standing at a position close to the object P while X-rays are irradiated, for example. In addition, an inspection engineer who operates the console device 30 may stay in the operators room on a steady basis. In the present specification, the term "operator" is used as a broader concept including the above-described surgeon and an inspection engineer.

The bed device 20 is a platform on which the object P as the imaging target is loaded, and includes a bed driver 21 and a table 22. The bed driver 21 moves the table 22 in the body axis direction of the object P by driving a motor under the control of the gantry controller 17, and inserts the object P into the opening of the gantry device 10. The table 22 is a board on which the object P is loaded.

The display 25 is installed in the examination room as a component separate from the gantry device 10. The display 25 is configured of a general display output device such as a liquid crystal display and an LED display. The display 25 displays the irradiation section, for example, in the same display aspect as the showing device 19 described below. In addition, the display 25 may display various types of information such as medical images in a manner similar to a console display unit 32 described below.

A sensor 26 is installed in the examination room and configured to detect a position of an operator (including a surgeon who performs a medical treatment on the object P). As the sensor 26, for example, a motion detection sensor configured to detect a human body by using camera images and a human detection sensor configured to detect a human body by using an electromagnetic wave such as infrared rays, visible light and ultrasonic waves may be used.

The console device 30 receives input of instruction by an operator and reconstructs an image from projection data acquired by the gantry device 10. Specifically, the console device 30 includes a console input circuit 31, the console display unit 32, a console control circuit 33, an image processing circuit 34, and an image data storage circuit 35.

The console input circuit 31 is configured as a mouse and a keyboard, for example. The console input circuit 31 is used by an operator for inputting an instruction to the X-ray CT apparatus 100. For example, the console input circuit 31 receives input of scan conditions. In addition, the console input circuit 31 may receive input of an irradiation section of a half scan in a manner similar to the gantry input circuit 18.

The console control circuit 33 includes processing circuitry and memory circuit. The processing circuitry of the console control circuit 33 is a processor configured to implement a function corresponding to each of programs stored in the memory circuit by executing each of the programs. Specifically, the console control circuit 33 implements an integrated control function, an acquisition control function, a reconstruction control function, and a setting function by executing the programs stored in the memory circuit.

The integrated control function of the console control circuit 33 controls the entirety of the X-ray CT apparatus 100 by controlling the gantry device 10, the bed device 20, and the console device 30. The acquisition control function of the console control circuit 33 controls the data acquisition circuit 14 so that the data acquisition circuit 14 acquires projection data generated by the X-ray detector 13. In addition, the reconstruction control function of the console control circuit 33 controls the image processing circuit 34 so that the image processing circuit 34 reconstructs image data from the projection data. Further, the setting function of the console control circuit 33 transmits setting information of imaging such as information on an imaging position and an imaging range and information on an irradiation section during a half scan, to the gantry controller 17. The console control circuit 33 can cause the console display unit 32 to display information inputted via the console input circuit 31.

For example, information on an irradiation section at the time of a half scan inputted via the gantry input circuit 18 by an operator such as a surgeon who performs a medical treatment on the object P is once inputted to the console control circuit 33, and then this information is set on the gantry controller 17 having the above-described imaging control function, by the setting function of the console control circuit 33.

Incidentally, the gantry controller 17 may implement a setting function equivalent to the setting function of the console control circuit 33, by executing the corresponding program stored in the memory circuit. In this case, information on imaging conditions such as an irradiation section at the time of a half scan inputted via the gantry input circuit 18 by an operator may be set on the gantry controller 17 by the setting function of the gantry controller 17, without interposing the console control circuit 33. Also in this case, it is preferable to input the setting contents to the console control circuit 33 equipped with the setting function so that the gantry controller 17 and the console control circuit 33 share the setting contents.

Next, a method of determining a position performed by an operator will be briefly explained.

Figure 2:
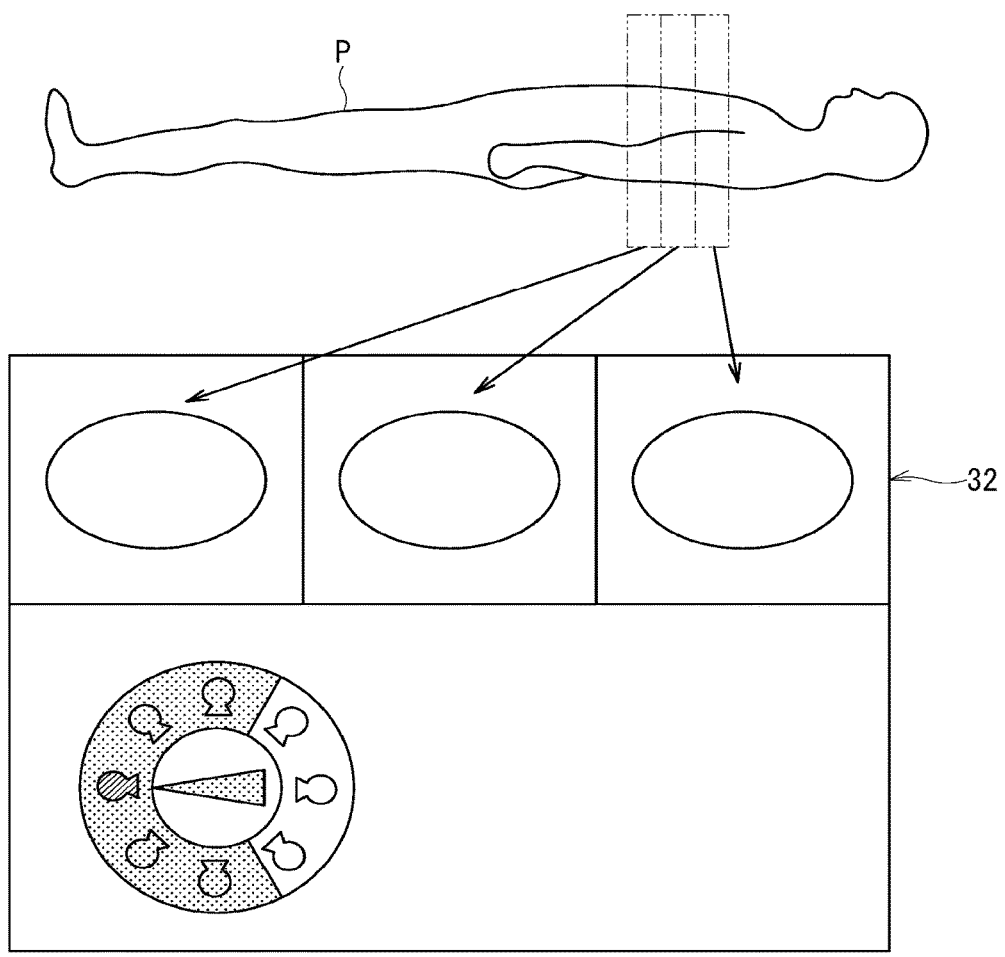
FIG. 2 is a schematic diagram showing an example of a method of determining a position of an operator in the first embodiment.

First, in order to specify the examination target region, an operator operates the X-ray CT apparatus 100 so that the X-ray CT apparatus 100 performs a scan such as a helical scan and a volume scan to acquire a CT image of the object P (see the middle part of FIG. 2). Next, the operator specifies the examination target region based on the acquired CT image, and determines the puncture position and the puncture direction in the case of paracentesis as an example. As a result, the standing position of a surgeon in paracentesis is determined. In this manner, an operator can determine a standing position during a medical treatment.

In addition, the X-ray CT apparatus 100 may be configured so that an operator can manually set an irradiation section via the gantry input circuit 18 or the console input circuit 31. Specifically, an operator can select one of the eight positions obtained by dividing the rotational orbit of the X-ray tube 12 into eight parts, as the center of a half scan so that X-ray exposure to himself or herself at the standing position during the medical treatment is reduced (see the bottom part of FIG. 2).

The setting function of each of the console control circuit 33 and the gantry controller 17 sets an irradiation section according to a position of an operator (including a surgeon who performs a medical treatment on the object P). A case where "the position of the operator" is "the standing position of the operator" will be explained as an example in the present specification. In this setting, an operator may input information on the standing position of the operator via the gantry input circuit 18 or the console input circuit 31. In this case, the setting function determines the standing position of the operator based on the inputted information on the standing position, and sets the irradiation section of X-rays to a section which is more distant from the distinguished standing position of the operator than other candidate sections so that exposure to the operator is reduced.

In addition, when the X-ray CT apparatus 100 includes the sensor 26, the setting function may determine the standing position of the operator based on an output signal from the sensor 26 and set the irradiation section of X-rays to a section being distant from the distinguished standing position of the operator so that exposure to the operator is reduced.

Moreover, information, by which a standing position of an operator can be distinguished, may be stored in the memory circuit of at least one of the console control circuit 33 and the gantry controller 17. In this case, the setting function may distinguish the standing position of the operator based on the information on how to distinguish a standing position of an operator stored in the memory circuit and may set the irradiation section of X-rays to a section being distant from the distinguished standing position of the operator so that exposure to the operator is reduced.

As the information on how to distinguish a standing position of an operator to be stored in the memory circuit, table data in which information on a surgeon who performs a medical treatment on the object P, information on examination contents, and information on a standing position are associated with each other, may be used, for example. A surgeon who performs a medical treatment on the object P sometimes determines his or her standing position depending on the examination contents. Consider a case where a certain examination is performed on the object P. In this case, if information on the examination contents and a surgeon who performs a medical treatment on this object P is obtained, the standing position of the surgeon can be estimated and determined by using the above-described type of table data.

The console display unit 32 is configured as a device such as a liquid crystal display and an LED display, and displays various types of information. For example, the console display unit 32 displays a GUI (Graphical User Interface) for receiving images stored in the image data storage circuit 35 and various types of instructions from an operator. In addition, the console display unit 32 displays scanned images used for planning a scan. Further, the console display unit 32 displays inputted contents as to patient information and imaging conditions being set to the console input circuit 31, when the console control circuit 33 instructs the console display unit 32 to display the above inputted contents.

The image processing circuit 34 is a processor configured to implement various types of processing on projection data, which are generated by the data acquisition circuit 14, by executing programs stored in the memory circuit. Specifically, the image processing circuit 34 performs preprocessing such as offset correction, logarithmic conversion, sensitivity correction, and beam hardening correction on the projection data acquired by the data acquisition circuit 14, reconstructs an image based on reconstruction conditions instructed from the console control circuit 33, and stores the reconstructed image in the image data storage circuit 35.

The image data storage circuit 35 is configured as, for example, a hard disc, an optical disc, or a semiconductor memory element such as an RAM (Random Access Memory), an ROM (Read Only Memory), and a flash memory, and stores images reconstructed by the image processing circuit 34.

The gantry input circuit 18 receives input of an irradiation section indicative of the section/span on the rotational orbit of the X-ray tube 12 through which X-rays are irradiated. As image reconstruction methods performed by the X-ray CT apparatus 100, a full scan and a half scan are included. In a full scan, projection data obtained by one full turn of the X-ray tube 12 around the object P, i.e. projection data obtained by rotating the X-ray tube 12 around the object P by approximately $2\pi$ [radian] are necessary for reconstructing CT image data of one volume. In a half scan, projection data obtained by rotating the X-ray tube 12 around the object P by approximately $\pi+\alpha$ [radian] are necessary for reconstructing CT image data of one volume, defining a fan angle as $\alpha$. Although the X-ray CT apparatus 100 of the present embodiment can perform both of a full scan and a half scan, setting of an irradiation section is assumed to be applicable to a half scan. As to the above irradiation section, it will be explained in detail by reference to FIG. 3 as follows.

Figure 3:
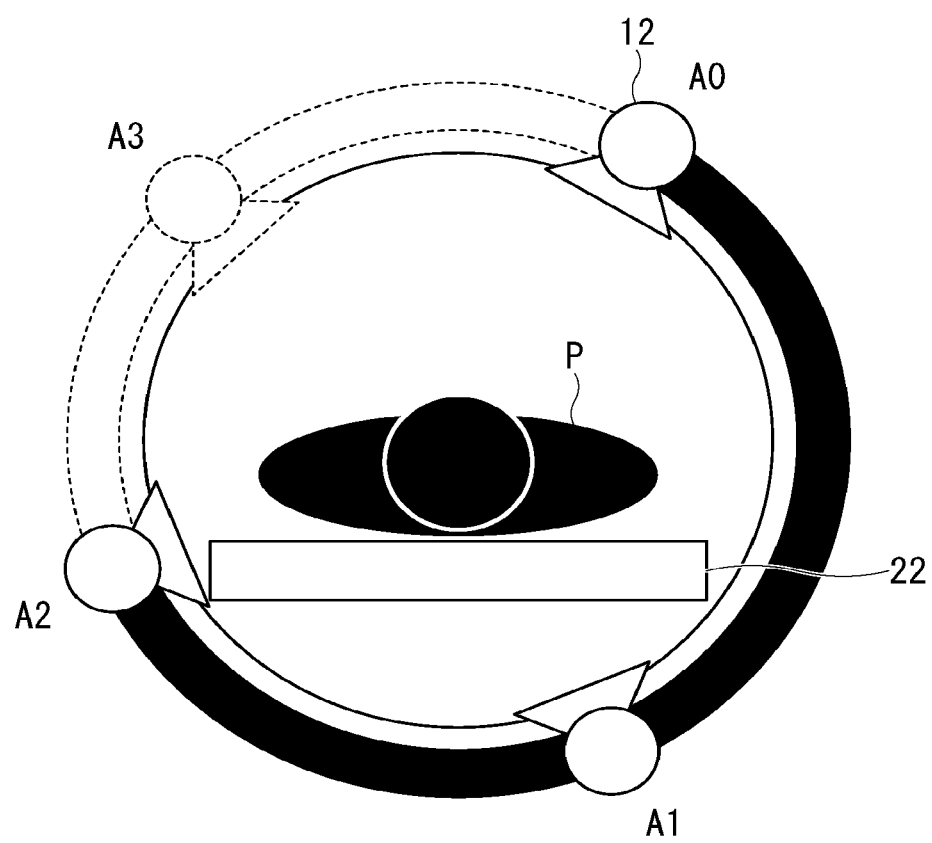
FIG. 3 is a schematic diagram showing an example of relationship between an X-ray tube and an irradiation section in the first embodiment.

FIG. 3 is a schematic diagram showing an example of positional relationship between the X-ray tube 12 and its rotational orbit in association with the object P during a scan. The X-ray tube 12 irradiates X-rays during the span shown by a black orbital belt in FIG. 3. For example, the X-ray tube 12 irradiates X-rays while being located at A0, A1, or A2, and the X-ray tube 12 does not irradiate X-rays while being located at A3. To be precise, the above-described irradiation section means a moving section of the X-ray detector 13 or an X-ray source such as the X-ray tube 12 on the rotational orbit during X-ray irradiation.

The imaging control function of the gantry controller 17 causes the X-ray tube 12 to radiate X-rays during the irradiation section based on the information on the irradiation section included in information of imaging conditions inputted via the console input circuit 31 and/or the gantry input circuit 18, and causes the X-ray tube 12 to stop irradiation except the irradiation section.

Figure 4:
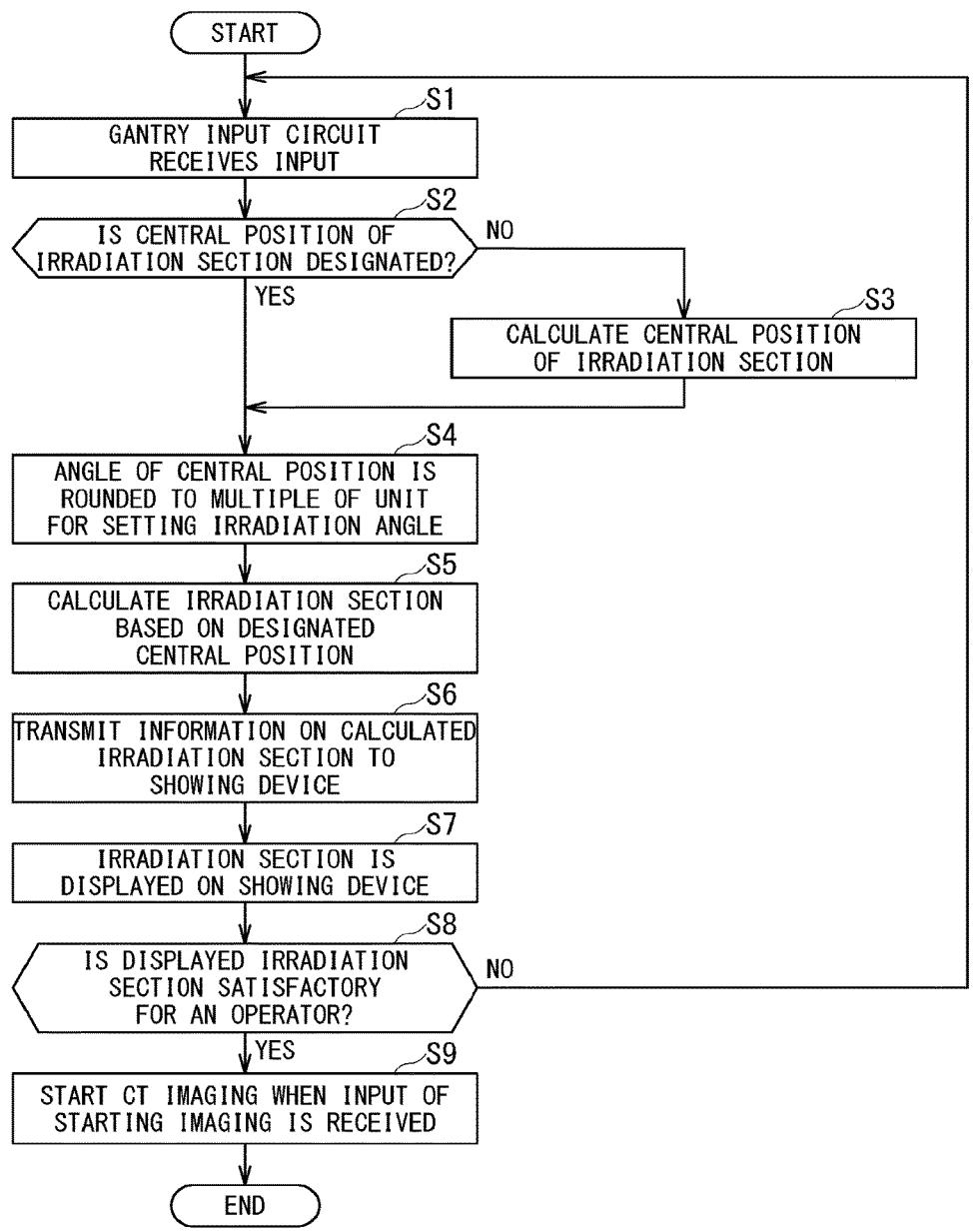
FIG. 4 is a flowchart showing an example of a flow of determining an irradiation section in the first embodiment.

The irradiation section is determined by designating the central position of the section or designating the angles at the start point and ending point of the section. The method of determining the irradiation section will be explained in detail by reference to the flowchart of FIG. 4 as follows.

First, in the step S1, the gantry input circuit 18 receives input contents entered by an operator. The irradiation section is designated by setting both angles of the start point and the ending point or setting the angle of the central position with the use of an input tool such as a GUI and a switch.

In the step S2, whether the central position of the irradiation section is designated or not is determined. When the central position of the irradiation section is designated, the processing proceeds to the step S4. When both angles of the start point and the ending point are designated, the processing proceeds to the step S3.

In the step S3, the central position of the irradiation section is calculated. Here, the rotational orbit can be divided into two arcs so that both ends of each of the two arcs become the above-described start point and the ending point. The central angle corresponding to the irradiation section should exceed 180 degrees in a half scan. Thus, the midpoint of the arc, whose central angle exceeds 180 degrees, out of the above two arcs is determined as the central position of the irradiation section.

In the step S4, the angle at the central position of the irradiation section inputted in the step S1 or calculated in the step S3 is rounded to a multiple of a unit for setting the irradiation angle. For example, when the irradiation angle can be set at intervals of 10 degrees and the angle at the central position of the irradiation section is calculated as 123 degrees, it is rounded to 120 degrees as the closest value of all the settable irradiation angles.

In the step S5, the irradiation section is calculated based on the designated central position.

Figure 5:
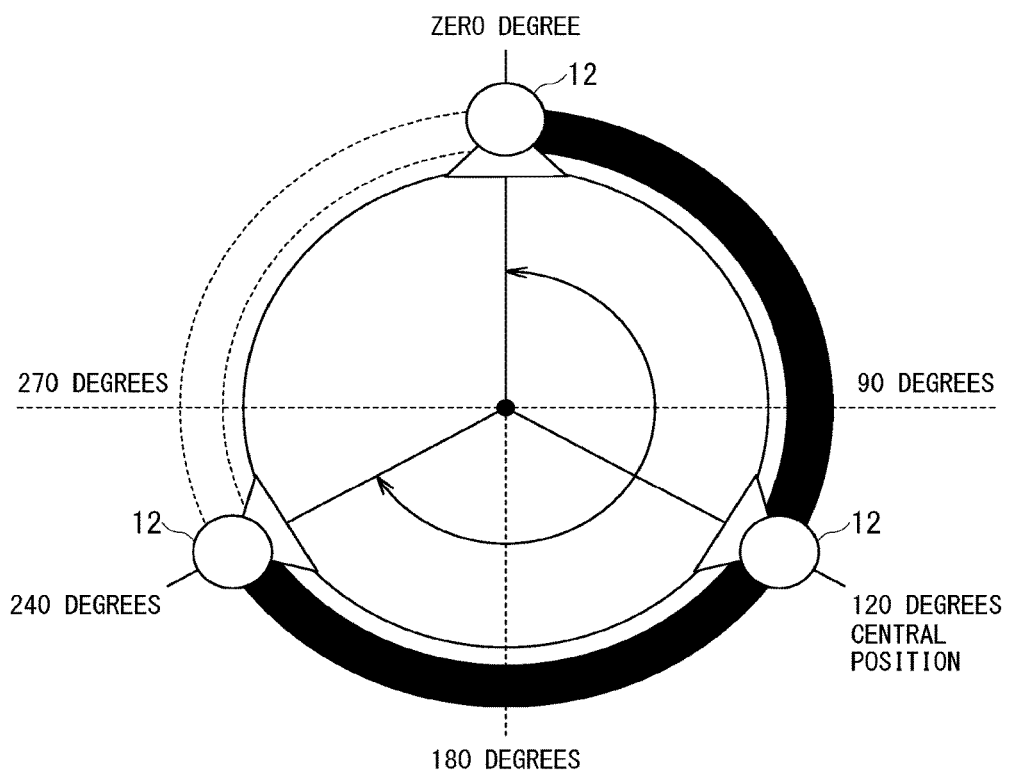
FIG. 5 is a schematic diagram showing an example of relationship between the central position and an irradiation section in the first embodiment.

FIG. 5 illustrates a case where the vertically upward direction in the opening is defined as zero degree of the rotational angle and the angle of the central position is set to 120 degrees. For example, when the fan angle of the X-ray CT apparatus 100 is 60 degrees, the rotational angle necessary for a half scan is 240 degrees. When the angle at the central position is 120 degrees, the irradiation section whose start point angle is zero degree, and whose ending point angle is 240 degrees, is set. Even if the start point and the ending point of the irradiation section are designated by the gantry input circuit 18, the start point and the ending point of the irradiation section are recalculated based on the calculated central position.

When the start point and the ending point of the irradiation section are inputted by an operator and the irradiation section calculated based on the inputted start point and ending point does not reach the rotational angle necessary for a half scan, the X-ray CT apparatus 100 can display a warning on the showing device 19 or automatically correct the incorrect irradiation section based on the input contents by reflecting the calculation result. In other words, when the angular range of the irradiation section calculated from conditions inputted by an operator is smaller than the angular range needed to obtain data required for reconstructing an X-ray CT image in a half scan, the warning may be displayed on the showing device 19.

Returning to FIG. 4, in the step S6, information on the calculated irradiation section is transmitted to the showing device 19. When it is required to display the central position of the irradiation section on the showing device 19, information on the central position may also be transmitted.

In the step S7, the showing device 19 displays the irradiation section. When the information on the central position of the irradiation section is also transmitted to the showing device 19, the showing device 19 may display the central position.

Incidentally, an example, in which the central position of the irradiation section is calculated and can be displayed on the showing device 19 in the case of designating the start point and the ending point of the irradiation section, has been explained in the steps S4 to S7. However, this is only one aspect of the present embodiment and calculation of the central position may be omitted in the above-described case. In this case, though the showing device 19 displays a warning if the irradiation section does not reach the angle necessary for a half scan, processing of automatically correcting the irradiation section may be omitted.

In the step S8, input to determine the irradiation section performed by an operator is received. When an operator sets the irradiation section again, the process returns to the step S1. When the irradiation section is satisfactory for the operator, the process proceeds to the step S9.

In the step S9, the X-ray CT apparatus 100 waits for input of a command to perform imaging by an operator. As soon as the X-ray CT apparatus 100 receives the above input, the X-ray CT apparatus 100 starts CT imaging based on the determined irradiation section.

The installation position of the gantry input circuit 18 is preferably such a position that a surgeon can reach and operate the gantry input circuit 18 with the hand from the standing position where the surgeon punctures a needle and/or puts the hand on the object P. In addition, foot pedals may be provided so that a surgeon can perform some of operations such as a command to start a scan with the foot when both hands are not free. Further, plural gantry input circuits 18 may be provided at respective positions such as the left side and the right side of the gantry device 10. This is so that a surgeon can touch and operate either of the gantry input circuits 18 with his or her hand regardless of which of the right or left side of the bed device 20 towards the opening of the gantry device 10 the surgeon stands at.

When the gantry input circuits 18 are provided at respective plural positions and an operator performs input to the X-ray CT apparatus 100 by using one of the gantry input circuits 18, it can be recognized that the operator stands at a position close to the gantry input circuit 18 by which the input was performed.

Figure 9:
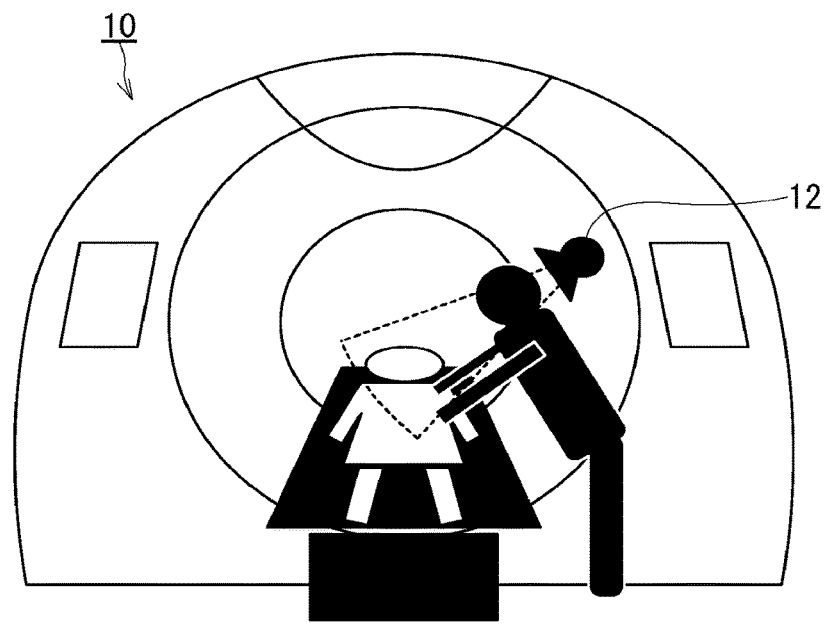
FIG. 9 is a schematic diagram showing an example of an aspect when an operator is positioned beside the X-ray tube during irradiation of X-rays, in the first embodiment.
Figure 10:
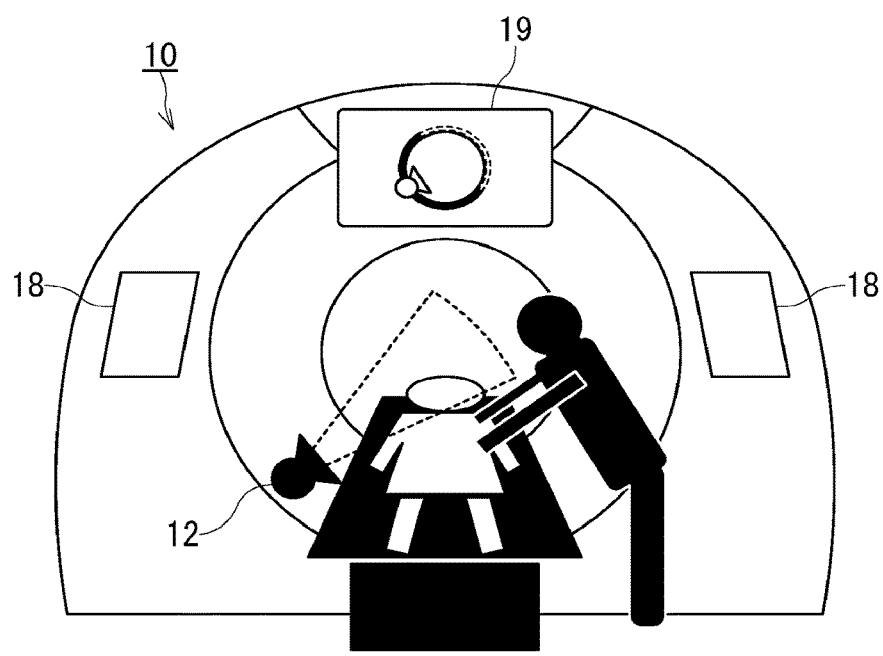
FIG. 10 is a schematic diagram showing an example of an aspect when an operator is positioned at a distance from the X-ray tube during irradiation of X-rays, in the first embodiment.

Accordingly, an irradiation section, with which exposure to an operator is estimated to be minimized out of all candidates for the irradiation sections, is proposed as a default setting section on the showing device 19 at the time of the above-described step S1 for setting an irradiation section, based on which gantry input circuit 18 received the input by the operator. For example, it is assumed that two gantry input circuits 18 are disposed on the respective right and left sides of the gantry device 10 as shown in FIG. 10. When an operator operates the gantry input circuit 18 of the right side under the above condition, it can be estimated that the operator stands at the right side and operates the gantry input circuit 18 of the right side. Since it is preferable that the operator is positioned away from the X-ray tube 12 during irradiation in order to reduce exposure, the irradiation section of X-rays is set such that the right side, i.e., the estimated standing position of the operator, is avoided as much as possible. Thereby, exposure to the operator is more reduced than the case of setting an irradiation section by which the X-ray tube 12 irradiates X-rays beside the operator as shown in FIG. 9.

When only one gantry input circuit 18 is provided, the irradiation section, with which X-ray exposure to an operator standing beside the gantry input circuit 18 is estimated to be smaller than other settable irradiation sections, may be proposed as a default setting section based on the position of the gantry input circuit 18 because the operator is expected to stand beside the only one gantry input circuit 18. As another example, when the gantry input circuit 18 receives input of information on imaging conditions by an operator after the console input circuit 31 received input of an arbitrary irradiation section, an irradiation section of X-rays, in which the standing position of the operator expected to stand beside the gantry input circuit 18 is avoided, may be proposed again.

Incidentally, when an operator changed the standing position, it is preferable to set the irradiation section again. As examples of such cases, a case where a surgeon performing a medical treatment on the object P changed his or her standing position during this medical treatment and the like are included.

For example, when a surgeon performed input by using one of plural gantry input circuits 18 during a medical treatment and exposure to this surgeon can be reduced by setting an irradiation section different from the current irradiation section, the setting function may set the irradiation section again. In addition, when the position of the surgeon is detected based on a detection signal of the sensor 26 and exposure to this surgeon can be reduced by setting an irradiation section different from the current irradiation section, the setting function may set the irradiation section again.

Figure 6:
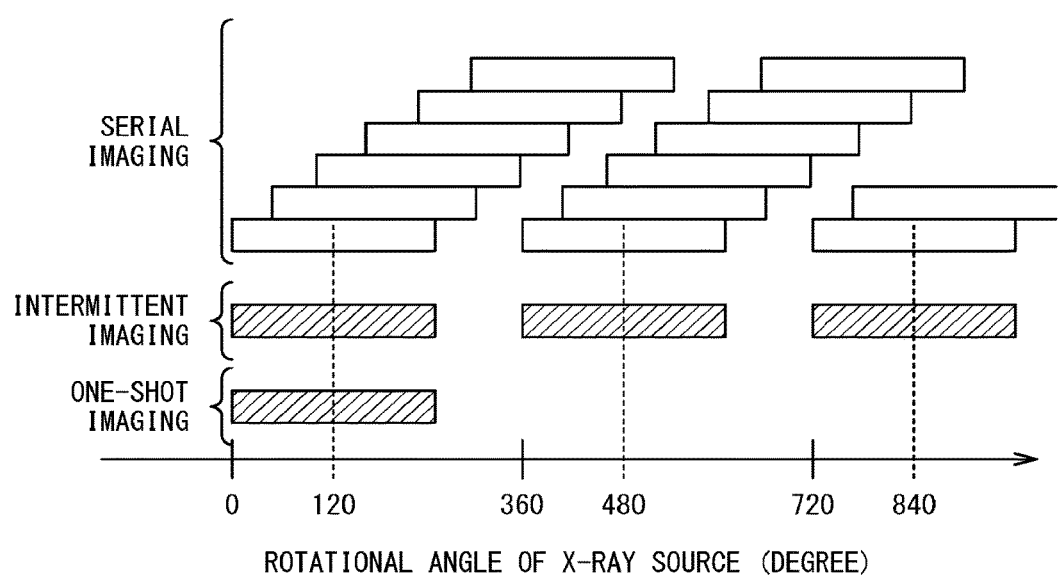
FIG. 6 is a schematic diagram showing an example of relationship between a rotational angle of an X-ray tube and each imaging method in the first embodiment.

As mentioned above, the X-ray CT apparatus 100 of the present embodiment can perform a full scan and a half scan. In a half scan, so-called one-shot imaging and intermittent imaging are included. The one-shot imaging is performed by irradiating and detecting X-rays while rotating the X-ray source by one turn, as to the irradiation section designated by the gantry input circuit 18. The intermittent imaging is performed by repeating radiation and detection of X-rays while rotating the X-ray source by one turn, plural times. FIG. 6 shows relationship between the irradiation section and the rotational angle of the X-ray tube 12. Each of the shadowed areas is a section during which X-rays are irradiated by setting the central position of the rotational angle to 120 degrees. When fluoroscopic imaging is performed at high frame rate in order to obtain cross-sectional images of the temporally changing object P, serial imaging in which X-rays are irradiated from all the angles is actually performed.

The gantry input circuit 18 may be equipped with a switch for switching between the respective imaging methods including the above-described one-shot imaging, intermittent imaging, and serial imaging. When the imaging mode is designated via the gantry input circuit 18, setting information including the designated imaging mode is transmitted to the gantry controller 17 and the gantry controller 17 performs imaging by controlling the high-voltage generator 11, the gantry driver 16, and the bed driver 21 so that the conditions of this imaging match the transmitted setting information. In addition, one or plural foot pedals may be provided around the gantry device 10 or the bed device 20 so that some or all of the operation of the gantry input circuit 18 can be performed with a foot.

Figure 7:
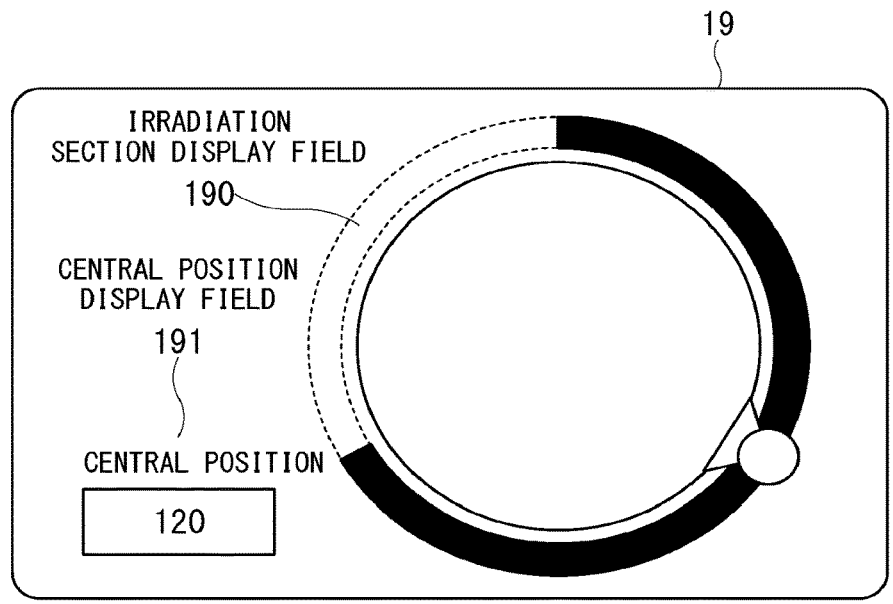
FIG. 7 is a magnified view of an example of a showing device in the first embodiment.

The showing device 19 displays an irradiation section. FIG. 7 shows a case where the showing device 19 is equipped with a display. The showing device 19 distinguishably displays the irradiation section by (a) displaying a circular ring in imitation of the rotational orbit of the X-ray tube 12 on an irradiation section display field 190 and (b) changing the display aspect of the part of the circular ring corresponding to the irradiation section, for example. As to changing the display aspect of the part of the circular ring corresponding to the irradiation section, it can be performed by coloring the corresponding part, for example.

In the central position display field 191, the central position of the irradiation section is displayed. A chart in imitation of the X-ray tube 12 may be additionally displayed on the central position of the irradiation section. Further, a schematic diagram of a human body indicating from which of the head side or the foot side the object P is inserted into the opening of the gantry device 10 may be displayed on the showing device 19. The showing device 19 is preferably disposed to such a position that a surgeon can immediately turn his or her eyes to the showing device 19 in order to visually recognize the irradiation section in a moment even while the surgeon is attaching the hand to the object P or puncturing a needle. When the showing device 19 includes a monitor, the monitor is disposed to the upper side of the opening part of the gantry device 10 as shown in FIG. 10.

Figure 8:
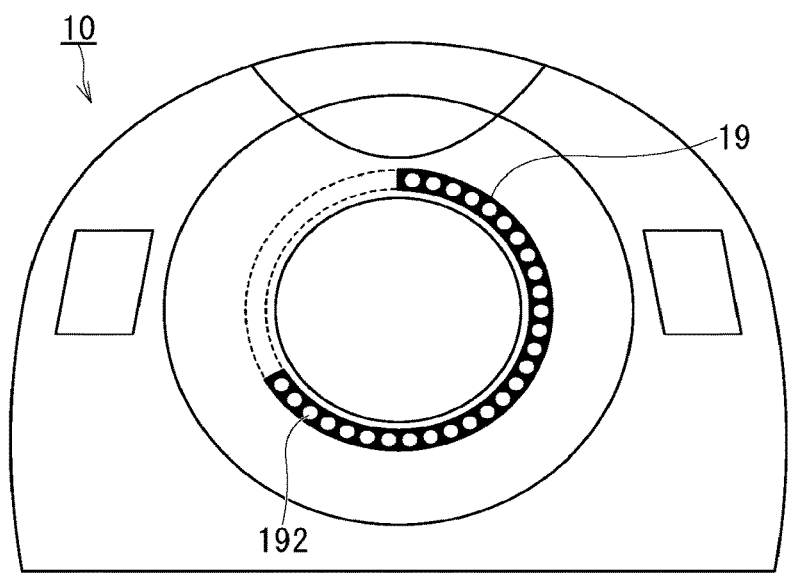
FIG. 8 is a planimetric diagram showing an example of disposing components of the showing device along the outer periphery of the opening of the gantry the in the first embodiment.

FIG. 8 shows a case where the showing device 19 includes an illumination 192 configured of light-emitting elements such as plural LEDs. The respective light-emitting elements of the illumination 192 are circularly arranged in imitation of the rotational orbit of the X-ray tube 12 on the outer circumference of the opening of the gantry device 10 or its adjacent area. The illumination 192 becomes luminous by switching some of its light-emitting elements to the light-emitting state in a manner such that the arc formed by connecting its light-emitting elements in the light-emitting state corresponds to the irradiation section.

The showing device 19 may perform multicolor display. In this case, the showing device 19 may change display color for each imaging method such as the above-describe one-shot imaging and intermittent imaging, and may change display color depending on whether X-rays are currently irradiated or not.

Figure 11A:
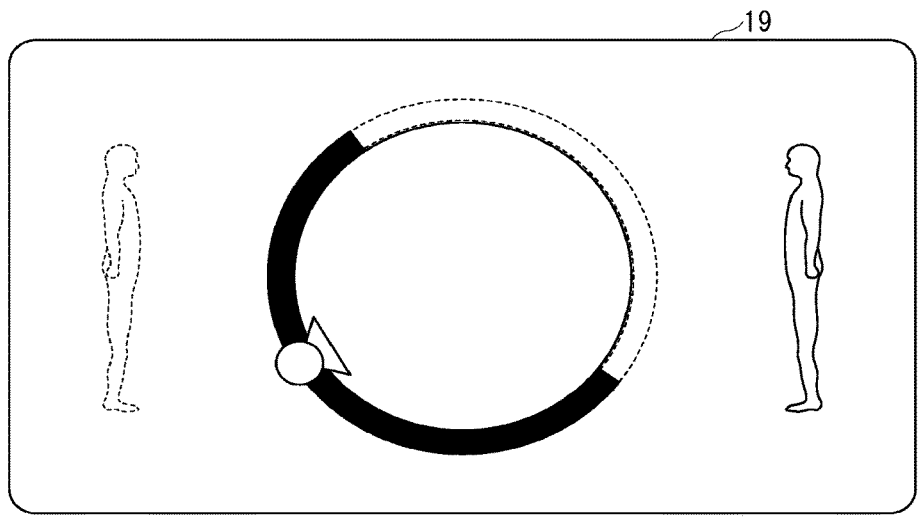
FIG. 11A is a schematic diagram showing an example of an image indicative of the position which minimizes exposure to an operator, in the first embodiment.
Figure 11B:
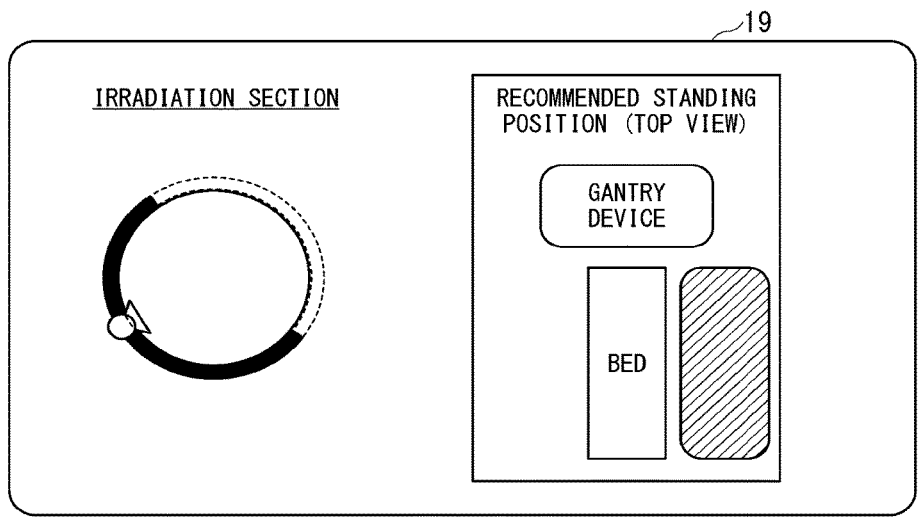
FIG. 11B is an explanatory diagram showing another example of an image indicative of the position which minimizes exposure to an operator, in the first embodiment.

FIG. 11A is an explanatory diagram showing an example of an image indicative of a standing position where exposure to an operator is relatively small. FIG. 11B is an explanatory diagram showing another example of an image indicative of a standing position where exposure to an operator is relatively small. FIG. 11A shows an example in which the recommended standing position is indicated as the side of the schematic human body shown by a solid line. In addition, FIG. 11B shows an example in which the recommended standing position is indicated as the shadowed area.

The showing device 19 may display a standing position where exposure to an operator is reduced, based on the irradiation section. In this case, the showing device 19 may display an image viewed from the body axis direction of the object P like FIG. 11A, or display an image viewed from the top side in the vertical direction like FIG. 11B. An operator can understand the standing position, where exposure to the operator is relatively small in the currently selected irradiation section, easily and accurately by referring to an image like FIG. 11A and/or FIG. 11B.

As mentioned above, the X-ray CT apparatus 100 of the first embodiment includes the gantry input circuit 18 configured to set an irradiation section (i.e., the section of irradiating X-rays on the rotational orbit of the X-ray tube 12) and the showing device 19 for confirming the irradiation section, around the opening part of the gantry device 10. Thereby, when an operator works near the object P during a half scan, the operator can avoid the side of the X-ray tube 12 in the irradiation state, which is very subject to scattered rays considered to be the main factor of exposure to an operator. In other words, there is a high possibility of increasing exposure to an operator if the operator stands beside the irradiation section of the X-ray tube 12 as shown in FIG. 9. However, if an operator can visually confirm the irradiation section of the X-ray tube 12 by the showing device 19 as shown in FIG. 10, the operator can judge the standing position where exposure is relatively small and a method of attaching the hand to the object P by which exposure can be reduced. When an operator cannot change his or her standing position and/or how to attach the hand, the operator can reduce exposure by setting the irradiation section of the X-ray tube 12 to a position distance from his or her standing position via the gantry input circuit 18.

Second Embodiment

Figure 12:
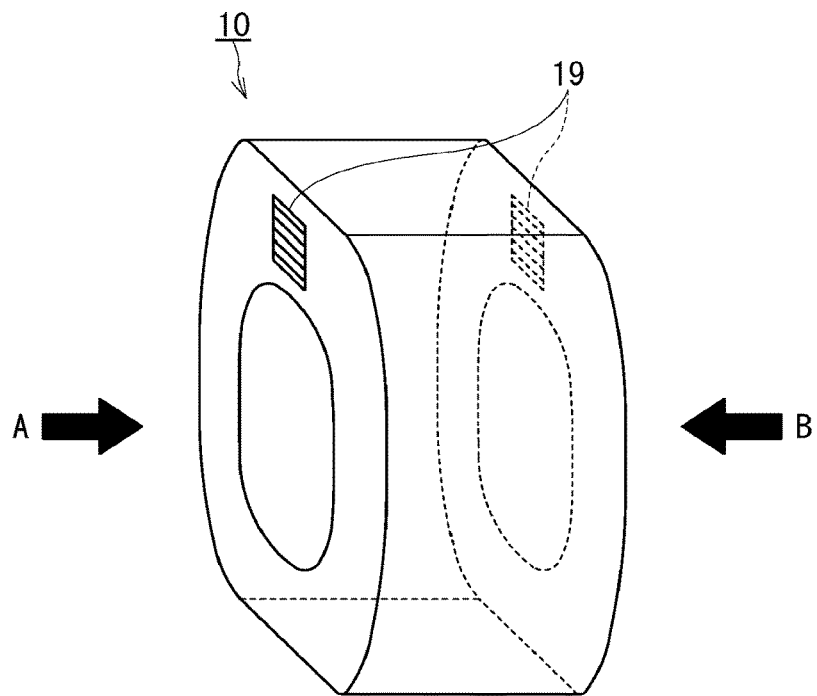
FIG. 12 is a schematic oblique diagram showing an example of providing plural showing devices on the gantry device, in the second embodiment.

As shown in FIG. 12, the X-ray CT apparatus 100 of the second embodiment includes two showing devices 19, each of which is the same as that of the first embodiment, and one and the other showing devices 19 are disposed on the frontal surface and back surface of the opening part respectively. The X-ray CT apparatus 100 of the second embodiment can insert the object P from both surfaces in each of which the opening of the gantry device 10 is formed, i.e., can insert the object P from both directions. Further, the X-ray CT apparatus 100 of the second embodiment can perform ordinary CT imaging and CT imaging during a medical treatment. As to the X-ray CT apparatus 100 of the second embodiment, the same reference numbers are given for identical components between the first and second embodiments, and duplicate explanation is omitted.

FIG. 12 shows only the gantry device 10, and the showing devices 19 are disposed on the respective two surfaces in each of which the opening of the gantry device 10 is formed. For the convenience of explanation, the direction A and the direction B are defined as shown by the respective arrows in FIG. 12.

Figure 13:
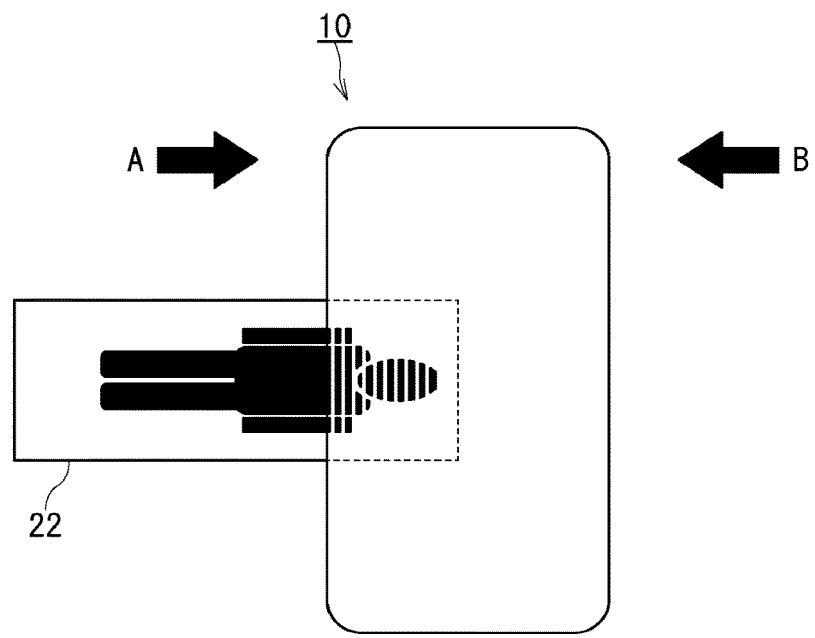
FIG. 13 is a schematic planimetric diagram showing an aspect of an object and the gantry device when viewed from the top, in the second embodiment.

FIG. 13 is a chart of the gantry device 10 viewed from the top side in the vertical direction. The directions A and B in FIG. 13 are the same as those shown in FIG. 12.

Figure 14:
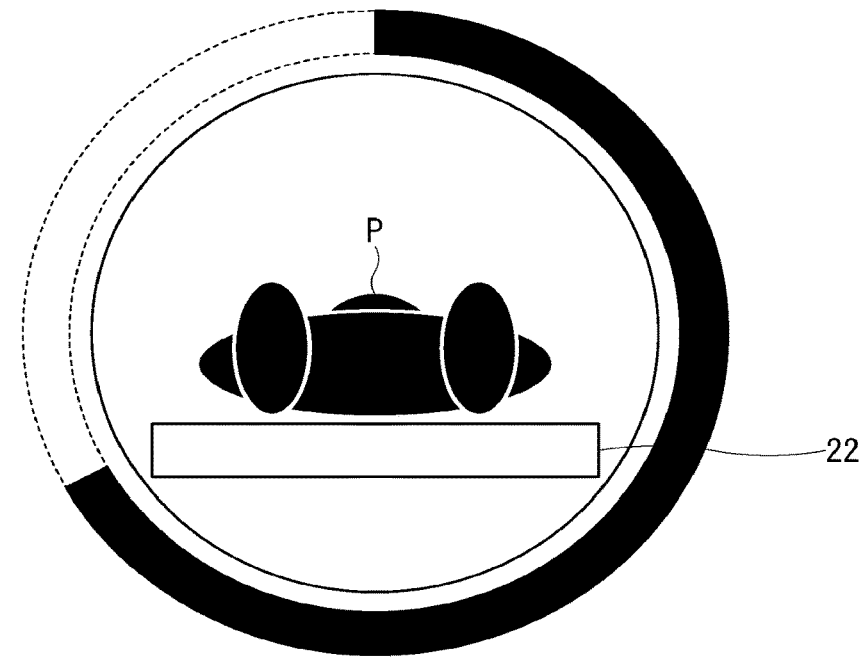
FIG. 14 is a schematic diagram showing an example of relationship between the object P and an irradiation section during a scan when viewed from the foot side, in the second embodiment.
Figure 15:
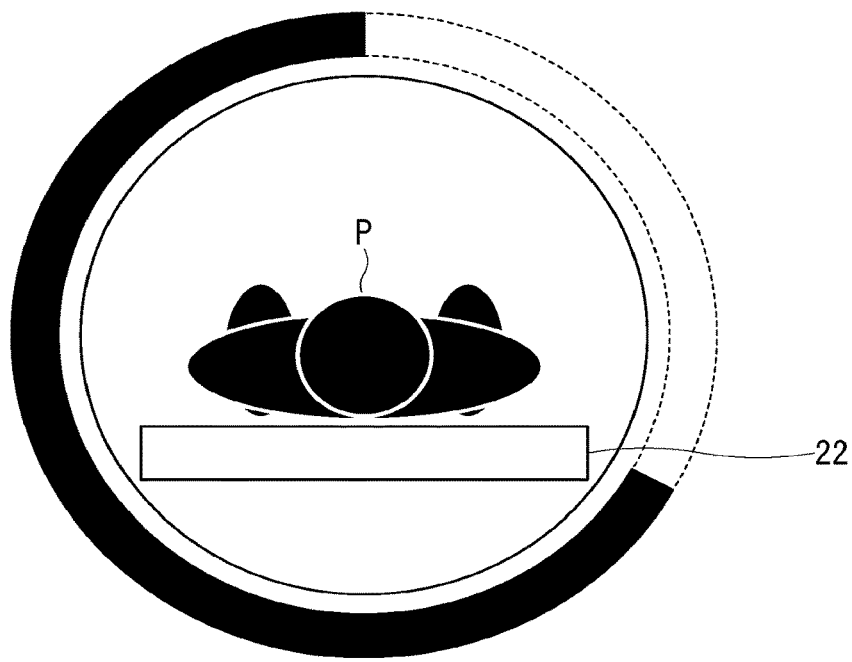
FIG. 15 is schematic diagram showing an example of relationship between the object P and an irradiation section during a scan when viewed from the head side, in the second embodiment.

Consider a case where the object P is moved from the head part in the direction A into the opening part, for example. When the irradiation section is set to the section shown by a black circular belt region in FIG. 14 viewed from the direction A (i.e., viewed from the bottom of the foot), the irradiation section viewed from the direction B (i.e., viewed from the head side of the object P) is mirror-reversed as shown in FIG. 15. In consideration of this principle, each of the two showing devices 19 displays the irradiation section so that the displayed irradiation section matches the irradiation section viewed from its installation surface.

Figure 16:
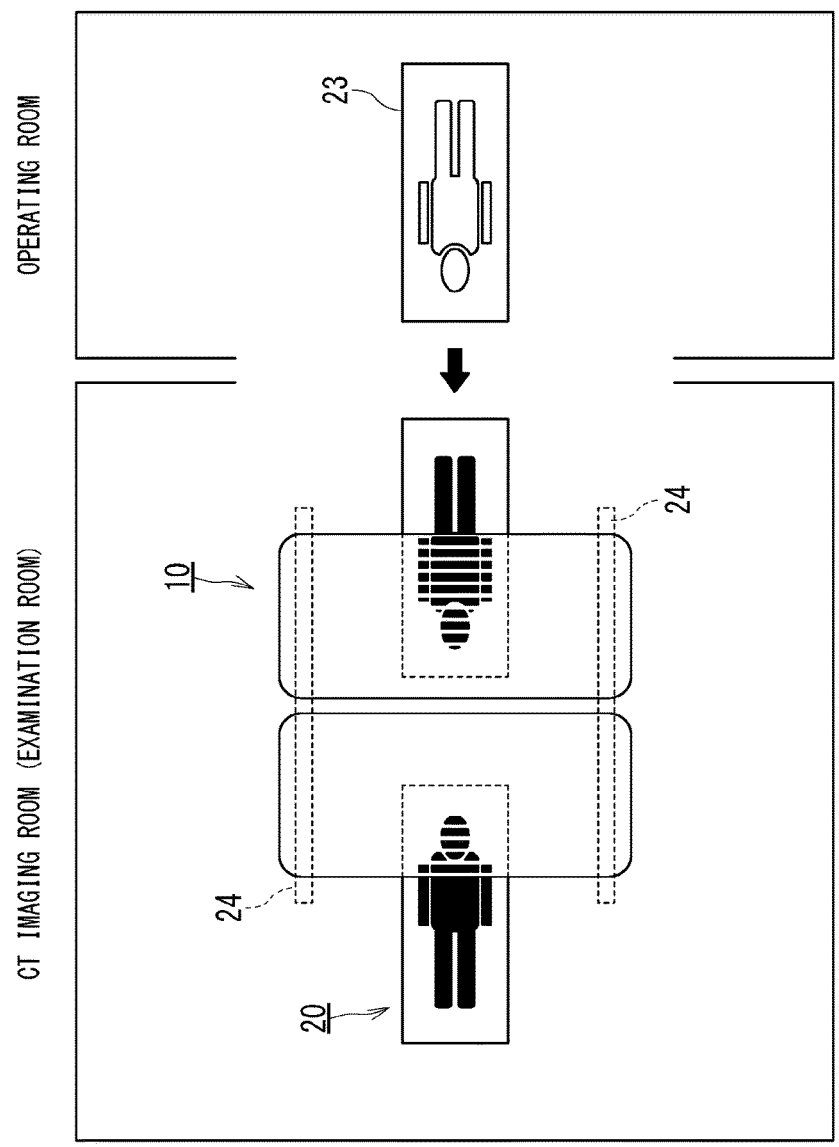
FIG. 16 is a schematic planimetric diagram showing an example of an aspect of moving an object into a CT imaging room during a medical treatment, in the second embodiment.

To dispose the showing devices 19 on the respective frontal and back sides of the opening of the gantry device 10 is advantageous, when the object P being subjected to a medical treatment in the operating room is moved to the CT imaging room and a CT scan is performed as shown in FIG. 16.

In general, an object is scanned by using the bed device 20 in the CT imaging room. In case where a CT scan is performed on the object P subjected to a medical treatment in the operating room, the object P subjected to the medical treatment is loaded on a movable bed 23 and then moved from the operating room to the CT imaging room juxtaposed with the operating room. Further, in this case, the object P is moved to one side of the opening of the gantry device 10 which is the opposite side with respect to the bed device 20 installed in the CT imaging room. Incidentally, the gantry device 10 can move along the rails 24 so that the movable bed 23 and the bed device 20 do not interfere with each other during the scan using the movable bed 23.

As mentioned above, the X-ray CT apparatus 100 of the second embodiment is equipped with the showing devices 19 on the respective two surfaces of the gantry device 10, in each of which the opening is formed. In addition, information on the irradiation section is appropriately displayed on each of the showing devices 19, in a different manner depending on the direction of the object P viewed from the installation surface of each of the showing devices 19. Thus, a surgeon can easily judge the standing position where exposure is relatively low and a manner of attaching hand to the object by which exposure is reduced, while working in a medical treatment. Moreover, time needed for confirming the irradiation section is shortened and time of the medical treatment of the object P can be shortened.

According to the X-ray CT apparatus and the gantry device of at least one of the above-described embodiments, the gantry device is equipped with the gantry input circuit configured to set an irradiation section (i.e., a section on the rotational orbit of the X-ray tube 12 during which X-rays are irradiated) and the showing device by which the irradiation section can be visually confirmed. Thus, when an operator works near the X-ray CT apparatus, the operator can judge the standing position where exposure is relatively low and a manner of attaching hand to the object by which exposure is reduced.

Although an example in which the setting function selects an irradiation section estimated to cause relatively low exposure to an operator has been explained above, this is only an example. Including this example, the setting function may set an irradiation section so as to reduce exposure at a position where an operator wishes to reduce X-ray exposure. For example, the setting function may set an irradiation section of X-rays so that exposure to a predetermined region and/or an examination target region of the object P is relatively reduced compared with other selectable irradiation sections.

In this case, as candidates for a setting reference of determining an irradiation section, (a) to reduce exposure to an operator by reducing exposure at the standing position of the operator, (b) to reduce exposure to a predetermined region of the object P, (c) to reduce exposure to an examination target region of the object P are at least included. A user may manually set the setting reference of determining an irradiation section by, for example, selecting one of the above (a), (b), or (c). Additionally, as to the setting reference of determining an irradiation section, priority order of the above (a), (b), and (c) may be preliminarily determined.

As predetermined regions of the object P where exposure should be reduced, regions susceptible to X-rays exposure such as crystalline lens and regions to which exposure should be avoided based on the past exposure record data such as dose tracking data are included. In addition, as examination target regions to which exposure should be reduced, regions where a device estimated to potentially become artifact in imaging can exist such as the region where a puncture needle is injected are included, for example.

The processing circuitry of each of the gantry controller 17 and the console control circuit 33 in the above-described embodiments is an example of the processing circuitry described in the claims.

In addition, the term "processor" used in the explanation of the gantry controller 17, the console control circuit 33, and the image processing circuit 34 means, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of a processor instead of storing programs in the memory circuit. In this case, the processor implements various types of functions by reading out programs stored in its own circuit and executing the programs.

Moreover, each function of the processing circuitry of each of the gantry controller 17 and the console control circuit 33 may be implemented by processing circuitry configured of a single processor. Further, the processing circuitry of each of the gantry controller 17 and the console control circuit 33 may be configured by combining plural processors independent of each other so that each function of the processing circuitry is implemented by causing each processor to execute the corresponding program.

When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray CT apparatus comprising:
an X-ray source configured to irradiate an object with X-rays;
an X-ray detector configured to detect X-rays radiated by the X-ray source and passed through the object;
processing circuitry configured to receive an instruction from an operator regarding an irradiation section which is a moving span through which the X-ray source or the X-ray detector moves during X-ray irradiation and to set the irradiation section in accordance with the instruction from the operator;
at least one showing device configured to display the irradiation section, the processing circuitry being configured to control the at least one showing device to display the irradiation section such that an entirety of the irradiation section is visible simultaneously;
an image processing circuit configured to generate an X-ray CT image based on data obtained by the X-ray detector during the X-ray irradiation through the irradiation section; and
a gantry device provided with the X-ray source, the X-ray detector, and the showing device.

2. The X-ray CT apparatus according to claim 1, wherein the at least one showing device is configured to display a position where X-ray exposure to the operator including a surgeon who performs a medical treatment on the object is reduced based on the irradiation section being set by the processing circuitry.

3. The X-ray CT apparatus according to claim 1, wherein the processing circuitry is configured to switch the X-ray source between an irradiation state and a non-irradiation state in such a manner that the X-ray source radiates X-rays only during the irradiation state.

4. The X-ray CT apparatus according to claim 1, wherein the irradiation section is a section where the X-ray source radiates X-rays during implementing a half scan on the object.

5. The X-ray CT apparatus according to claim 1, wherein the at least one showing device includes a display, and the display is configured to display the irradiation section by a diagram obtained by dividing a circular ring in a circumferential direction.

6. The X-ray CT apparatus according to claim 1, wherein the at least one showing device includes a plurality of light-emitting elements circularly arranged on outer circumference of an opening of the gantry device or arranged around the opening of the gantry device, and is configured to switch some of the plurality of light-emitting elements to a light-emitting state in such a manner that an arc formed by the some of the plurality of light-emitting elements in the light-emitting state corresponds to the irradiation section.

7. The X-ray CT apparatus according to claim 1, wherein the at least one showing device comprises two showing devices,
each of the two showing devices is configured to display the irradiation section,
the gantry device has two surfaces, in each surface an opening is formed, and
the two showing devices are disposed on the respective two surfaces.

8. The X-ray CT apparatus according to claim 1, wherein the at least one showing device is configured to display a warning when an angular range of the irradiation section is smaller than an angular range needed to reconstruct an X-ray CT image.

9. The X-ray CT apparatus according to claim 1, further comprising a display installed independent of the gantry device in a room where the gantry device is installed, wherein the display is configured to display the irradiation section by a diagram obtained by dividing a circular ring in a circumferential direction.

10. The X-ray CT apparatus according to claim 4, wherein the processing circuitry is configured to cause the X-ray source to radiate X-rays based on an imaging mode of one of serial imaging, one-shot imaging, and intermittent imaging.

11. An X-ray CT apparatus comprising:
an X-ray source configured to irradiate an object with X-rays;
an X-ray detector configured to detect X-rays radiated by the X-ray source and passed through the object;
processing circuitry configured to set an irradiation section, which is a moving span through which the X-ray source or the X-ray detector moves during X-ray irradiation, according to a position of an operator including a surgeon who performs a medical treatment on the object;
at least one showing device configured to display the irradiation section, the processing circuitry being configured to control the at least one showing device to display the irradiation section such that an entirety of the irradiation section is visible simultaneously;
an image processing circuit configured to generate an X-ray CT image based on data obtained by the X-ray detector during the X-ray irradiation through the irradiation section; and
a gantry device provided with the X-ray source, the X-ray detector, and the showing device.

12. The X-ray CT apparatus according to claim 11, wherein
the gantry device includes at least one gantry input circuit configured to receive an instruction from the operator; and
the processing circuitry is configured to set the irradiation section according to an installation position of the at least one gantry input circuit.

13. The X-ray CT apparatus according to claim 11, further comprising an input circuit configured to receive an instruction from the operator, wherein
the processing circuitry is configured to set the irradiation section according to the position of the operator based on information on the position of the operator inputted to the input circuit.

14. The X-ray CT apparatus according to claim 11, further comprising at least one of a human detection sensor and a camera, and wherein
the processing circuitry is configured to set the irradiation section according to the position of the operator based on output signal of the human detection sensor or the camera.

15. The X-ray CT apparatus according to claim 11, further comprising a memory circuit configured to store position information used for determining the position of the operator, wherein
the processing circuitry is configured to set the irradiation section according to the position of the operator determined based on the position information stored in the memory circuit.

16. The X-ray CT apparatus according to claim 11, further comprising an input circuit configured to receive an instruction from the operator, wherein the gantry device is further provided with the input circuit.

17. The X-ray CT apparatus according to claim 12,
wherein at least one gantry input circuit comprises a plurality of gantry input circuits, each being configured to receive the instruction from the operator; and
the processing circuitry is configured to recognize a gantry input circuit which receives the instruction out of the plurality of gantry input circuits, and to set the irradiation section such that X-ray exposure to the operator positioned beside the gantry input circuit receiving the instruction is reduced.

18. A gantry device comprising:
an X-ray source configured to irradiate an object with X-rays;
an X-ray detector configured to detect X-rays radiated by the X-rays source and passed through the object; and
a showing device configured to display an irradiation section, which is a moving span through which the X-rays source or the X-ray detector moves during X-ray irradiation, such that an entirety of the irradiation section is visible simultaneously.

19. An X-ray CT method comprising:
receiving, using circuitry, an instruction from an operator regarding an irradiation section which is a moving span through which an X-ray source or an X-ray detector moves during X-ray irradiation;
setting, using the circuitry, the irradiation section in accordance with the instruction from the operator;
displaying the irradiation section such that an entirety of the irradiation section is visible simultaneously;
performing the X-ray irradiation; and
generating an X-ray CT image based on data obtained by the X-ray detector during the X-ray irradiation through the irradiation section.

* * * * *